United States Patent
Peebles

(10) Patent No.: US 9,506,842 B2
(45) Date of Patent: Nov. 29, 2016

(54) VOLUMETRIC SAMPLE ADJUSTMENT ASSEMBLY LOCATED OUTSIDE A LIQUID PROCESS LINE

(71) Applicant: Welker, Inc., Sugar Land, TX (US)

(72) Inventor: Tracy D. Peebles, Houston, TX (US)

(73) Assignee: Welker, Inc., Sugar Land, TX (US)

( * ) Notice: Subject to any disclaimer, the term of this patent is extended or adjusted under 35 U.S.C. 154(b) by 341 days.

(21) Appl. No.: 14/315,849

(22) Filed: Jun. 26, 2014

(65) Prior Publication Data

US 2015/0000427 A1 Jan. 1, 2015

Related U.S. Application Data

(60) Provisional application No. 61/839,993, filed on Jun. 27, 2013.

(51) Int. Cl.
*G01N 1/20* (2006.01)

(52) U.S. Cl.
CPC ....... *G01N 1/2035* (2013.01); *G01N 2001/205* (2013.01)

(58) Field of Classification Search
CPC .................... G01N 2001/2057; G01N 1/2035
USPC ............................................ 73/863.41, 61.59
See application file for complete search history.

(56) References Cited

U.S. PATENT DOCUMENTS

| | | | | |
|---|---|---|---|---|
| 3,746,217 A | * | 7/1973 | Hanset | G01N 35/1095 222/318 |
| 3,827,305 A | * | 8/1974 | Gilson | B01L 3/0224 222/43 |
| 4,760,881 A | * | 8/1988 | Long | E21B 49/082 166/165 |
| 5,650,124 A | * | 7/1997 | Gilson | B01L 3/0224 422/180 |
| 2004/0250377 A1 | * | 12/2004 | Park | E05F 3/20 16/50 |
| 2010/0319468 A1 | * | 12/2010 | Peebles | G01N 1/2247 73/863.12 |
| 2011/0192237 A1 | * | 8/2011 | Bombulie | G01N 1/10 73/863.11 |
| 2013/0000391 A1 | * | 1/2013 | Khuzwayo | G01N 1/16 73/61.59 |
| 2013/0036800 A1 | * | 2/2013 | Mohajer | G01N 1/2035 73/61.59 |

* cited by examiner

*Primary Examiner* — Eric S McCall
*Assistant Examiner* — Mohammed E Keramet-Amircolai
(74) *Attorney, Agent, or Firm* — Husch Blackwell LLP

(57) ABSTRACT

A volumetric sample adjustment assembly located outside of a process line to facilitate rapid changes in the sample volume without having to remove the sampler from the process line, from process pressure or without having to manually disassemble the collection head assembly, like some prior art devices. The volumetric sample adjustment assembly has a "gross adjustment" assembly to vary the gross sample volume within the predetermined range. This gross adjustment assembly uses a removable pin to vary the sample size. This removable adjustment pin may be removed and replaced in different positions to change the gross volume of the sample on short notice and without having to remove the sampler from the process line, from process pressure or without having to manually disassemble the collection head assembly.

33 Claims, 16 Drawing Sheets

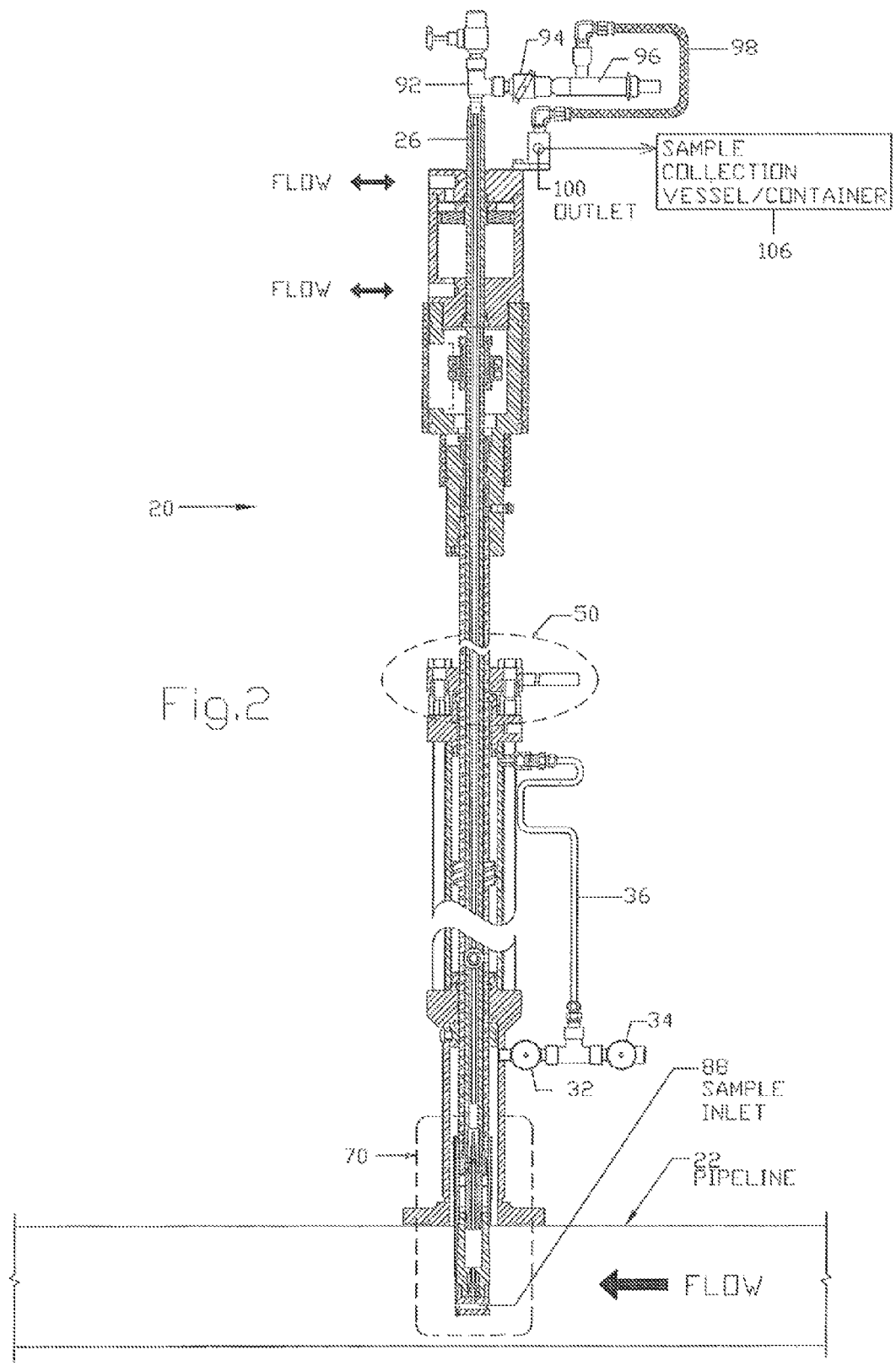

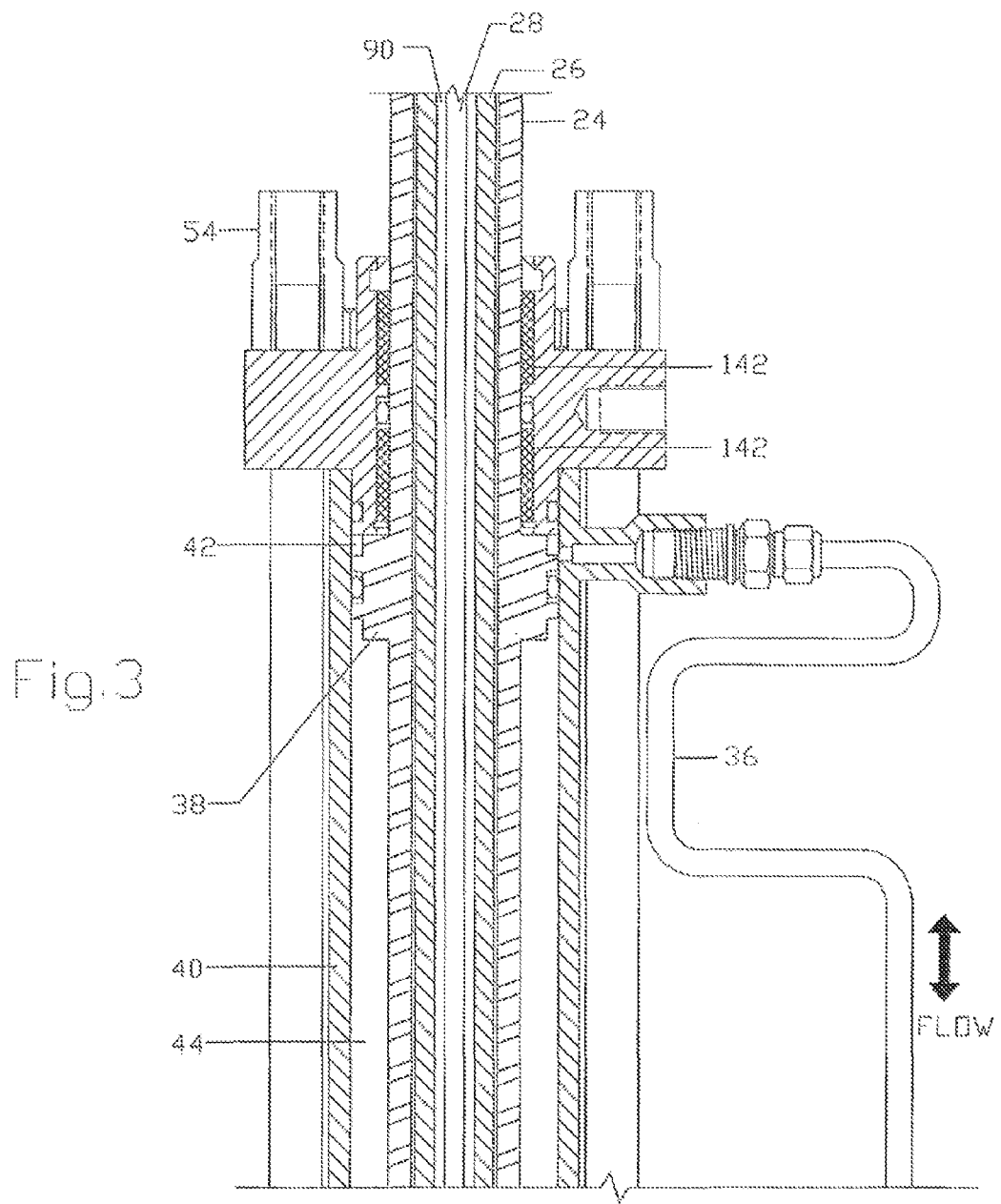

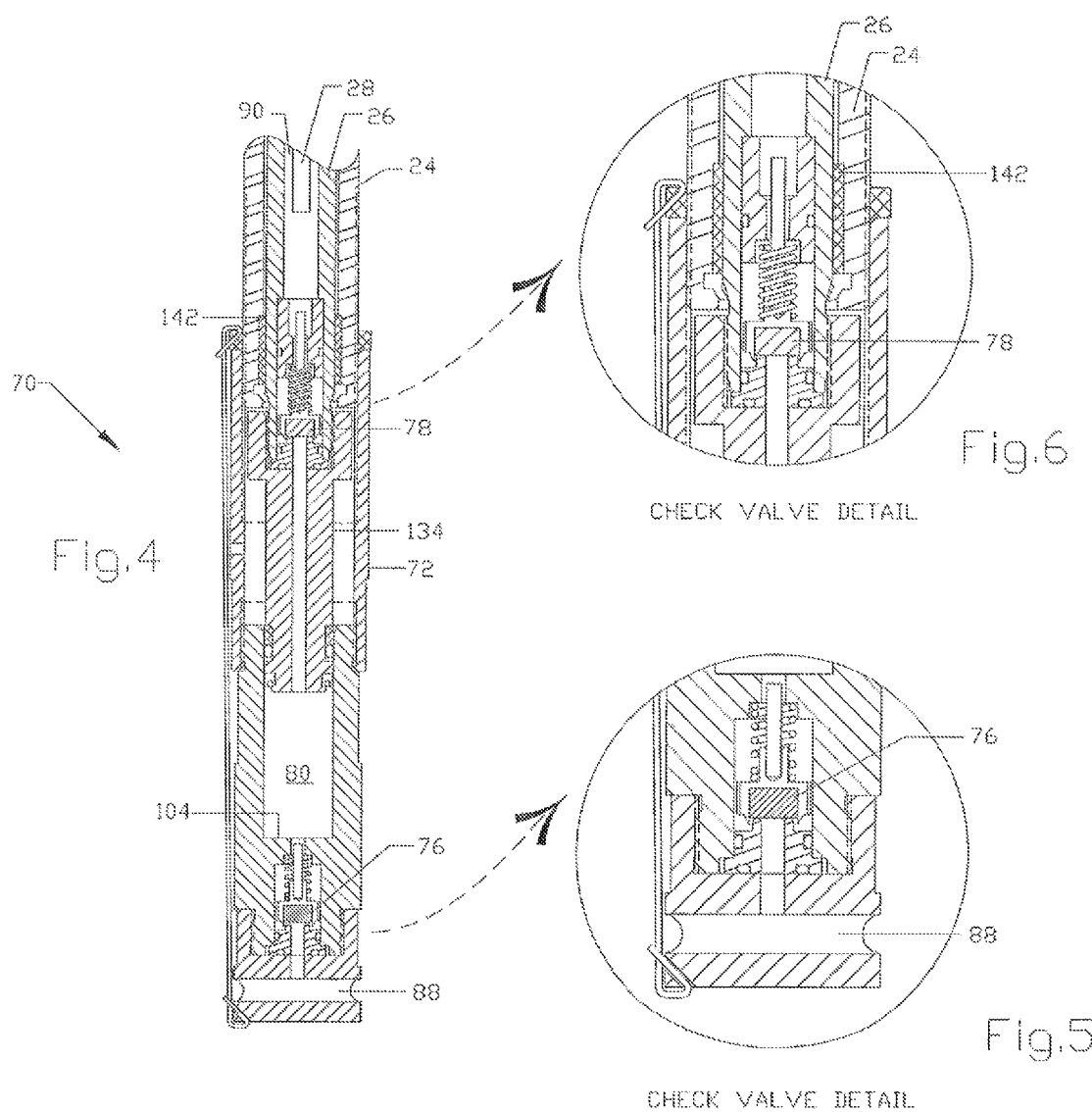

CHECK VALVE FLOW PATH

CHECK VALVE FLOW PATH

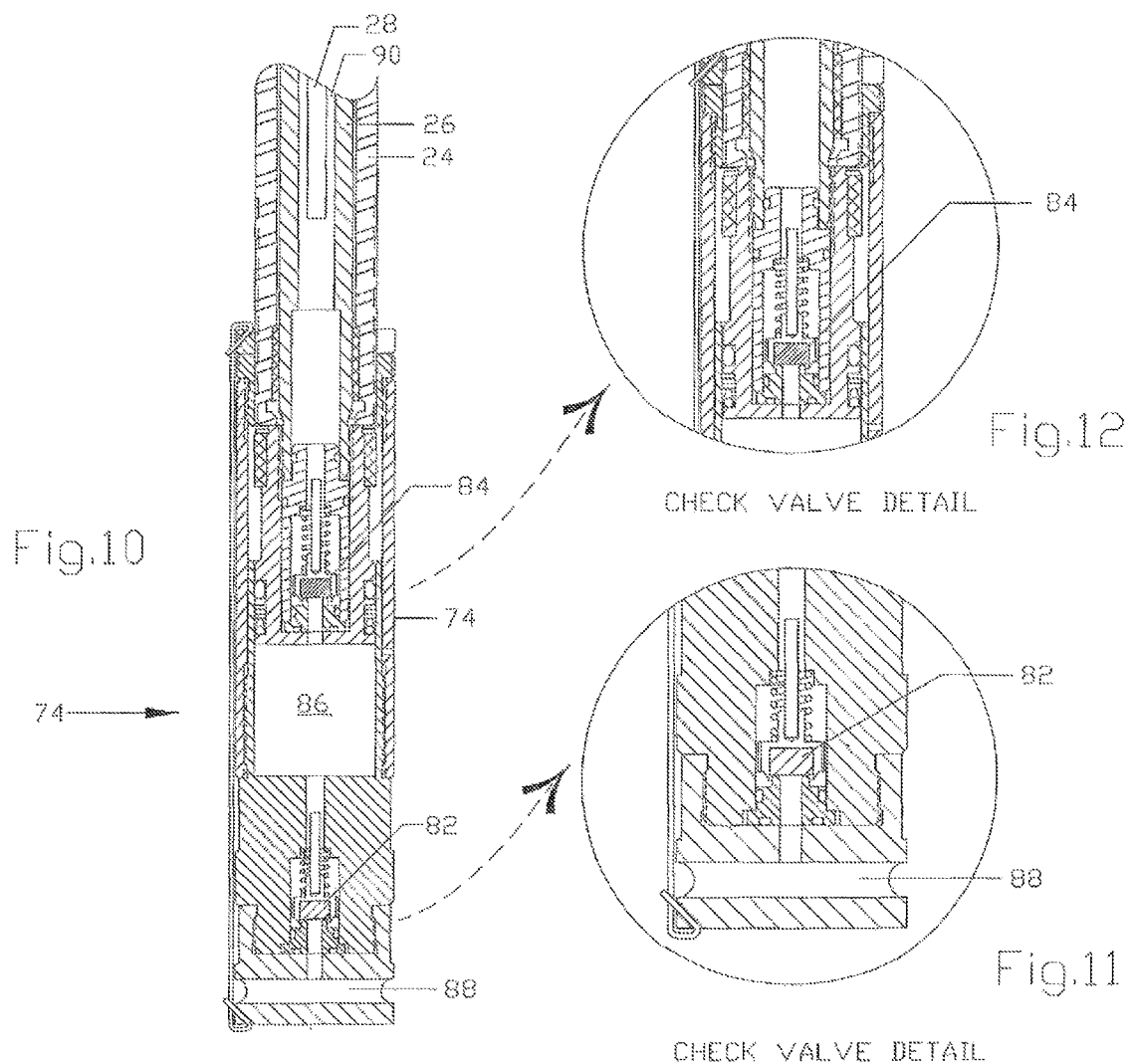

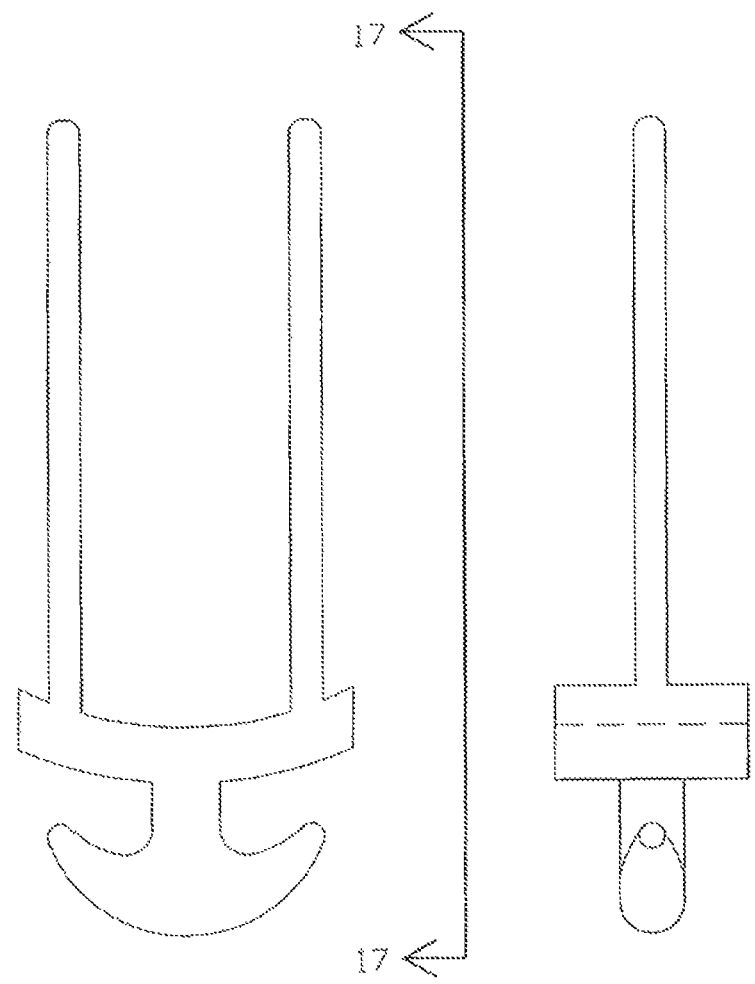

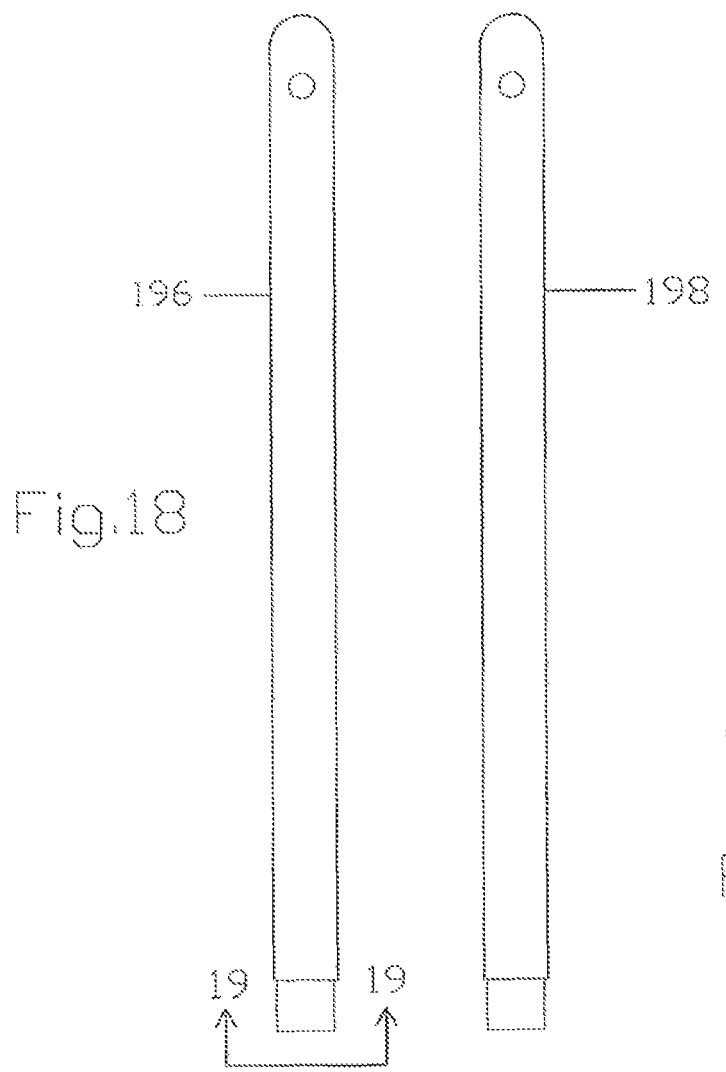

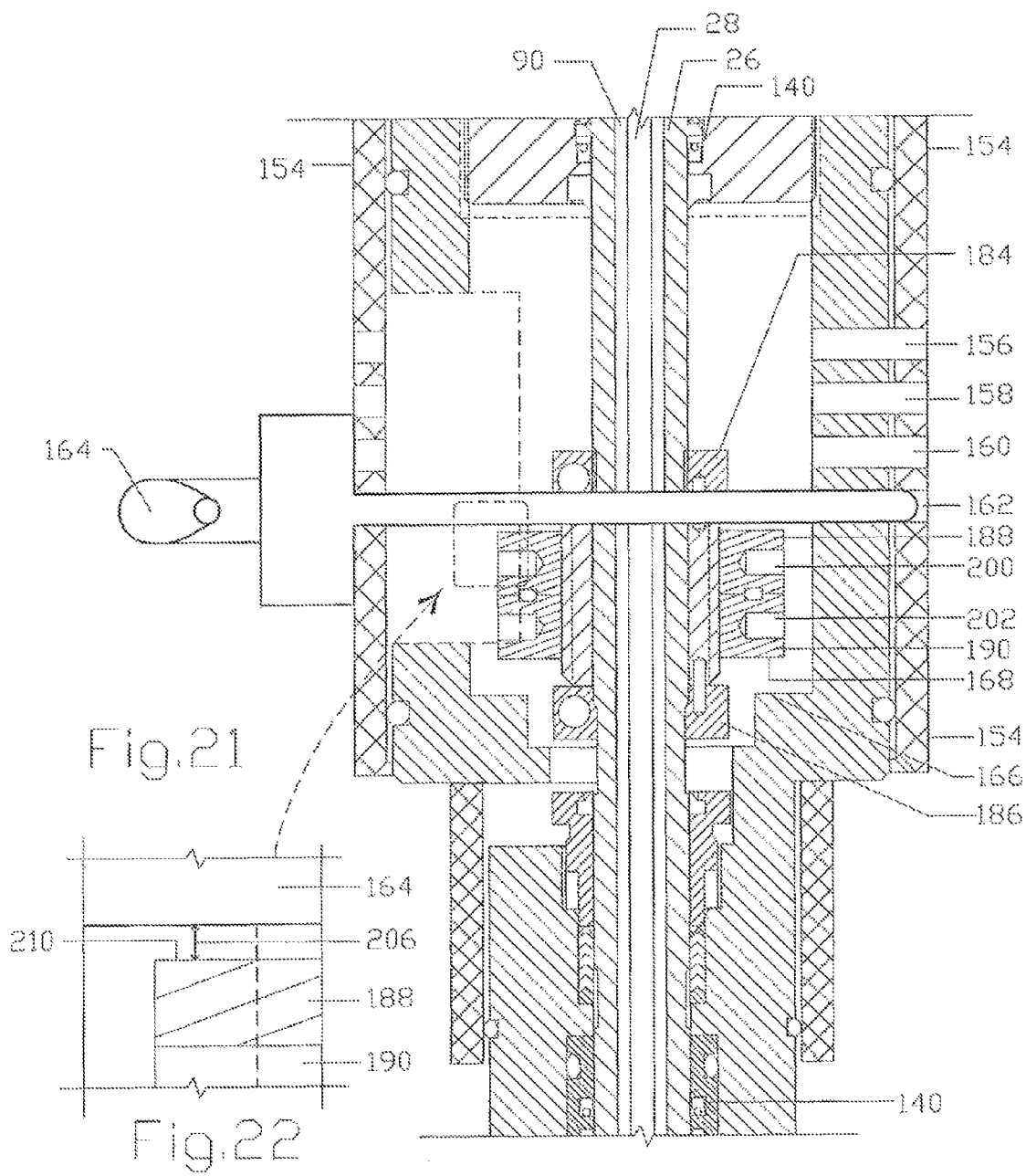

VOLUMETRIC SAMPLE ADJUSTMENT ASSEMBLY LOCATED OUTSIDE A LIQUID PROCESS LINE

CROSS REFERENCE TO RELATED APPLICATIONS

The present application claims priority to and incorporates herein by reference U.S. Provisional Patent Application Ser. No. 61/839,993 filed on Jun. 27, 2013.

BACKGROUND OF THE INVENTION

Samplers are used to take periodic samples from liquids flowing through a process line, e.g. a pipeline. Such liquids include water, crude oil, refined products including: gasoline, diesel, jet fuel, kerosene, etc., natural gas liquids including: liquid ethane, liquid propane, liquid butane, liquid iso-butane, etc. These samplers typically move a shaft up and down to take a sample which is then accumulated with prior samples in a sample collection container or vessel. This movement is sometimes referred to as a "stroke" in the industry. Further, some samplers are inserted and withdrawn from a process line through an isolation valve while the process line remains under pressure and in operation. In some of these samplers, the sample collection head assembly could be adjusted to vary the volume of sample, but this required removal of the sampler from the process line, removal from process pressure and manual disassembly of the sample head assembly which was time consuming, expensive and disruptive to the sample collection process. There is a need to be able to adjust the volume of a sample while the sampler is under process line pressure and while the process line is in operation.

Some liquid pipelines sequentially transport product from different customers and/or from different storage tanks. In one example, switching from different sources of product may occur as frequently as every 105 seconds to intervals as long as three days. Obviously, the switching interval varies and can vary widely beyond the intervals mentioned above.

Some sampling operations take seven liters of sample from each aliquot of product flowing through the line. If the switching interval is long, the volume of sample taken during each stroke of the sampler will be comparatively small. If the switching interval is short, the volume of sample taken during each stroke of the sampler with be comparatively large, in order to accumulate seven liters of sample. There is a need to be able to quickly and easily adjust the volume of sample taken during each stroke of the sampler, without delay or down time and without having to manually disassemble the sample head assembly.

SUMMARY OF THE INVENTION

The present invention is a volumetric sample adjustment assembly located outside of a process line to facilitate rapid changes in the sample volume without having to remove the sampler from the process line, from process pressure or without having to manually disassemble the collection head assembly, like some prior art devices. The present invention is sometimes referred to as an "external" sampler because the sample adjustment assembly is located external of the process line. The external sample volume adjustment assembly can be designed to operate within a predetermined range which is usually set by the customer and/or the specific application. For example, one predetermined range could be from near zero to 11 cc. As another example, the predetermined range could be from near zero to 24 cc. Other ranges may be suitable for different applications.

The volumetric sample adjustment assembly has a "gross adjustment" assembly to vary the gross sample volume within the predetermined range. This gross adjustment assembly uses a removable pin to vary the sample size. This removable adjustment pin is external to the process line and the sampler; further, the adjustment pin may be removed and replaced in different positions to change the gross volume of the sample on short notice and without having to remove the sampler from the process line, from process pressure or without having to manually disassemble the collection head assembly. For example, if the predetermined sample range is from near zero to 11 cc, the gross sample size may be easily changed from 2 cc, to 5 cc, to 8 cc to 11 cc by removal and placement of the adjustment pin in different positions in the gross adjustment assembly. The removable adjustment pin and the gross adjustment assembly are fast and easy to use and are economical to produce.

The present invention may, as an option, also include a "fine adjustment" assembly to make fine adjustments in the sample volume. This fine adjustment assembly is external to the process line; further, it may be adjusted without having to remove the sampler from the process line, from process pressure or without having to manually disassemble the collection head assembly. For example, if the predetermined sample volume is 11 cc, the sample volume could be adjusted to range from 2.5 cc, to 5.5 cc, to 8.5 cc to 11 cc. Other sample volumes may be set using the fine adjustment assembly, e.g. 0.5 cc, to 3.5 cc, to 6.5 cc to 9.5 cc. The fine adjustment assembly includes an O-ring which is positioned between a pair of opposing locking rings all of which surround a barrel connected to a middle shaft. Rotation of the opposing locking rings up or down the barrel "fine adjusts" to the volume of the sample. The gross adjustment assembly and the fine adjustment assembly cannot increase the predetermined range. But the predetermined range can be changed to, for example, near zero to 24 cc by removal of the sampler from the pipeline and disassembly of the sample head assembly. If required, both the gross adjustment assembly and the fine adjustment assembly may be combined in the volumetric sample adjustment assembly. Or the volumetric sample adjustment assembly may only include the gross adjustment assembly, depending on the application or the customer's wishes.

In this application, the term "down" will refer to movement towards the pipeline or devices/components proximate the pipeline. The term "up" will refer to movement away from the pipeline and devices/components opposite the pipeline. The sampler of this invention strokes "down" to take a sample and strokes "up" to replenish fluid in a variable volume sample chamber. A complete cycle is one stroke down and one stroke up. The distance of the up stroke of the sample head may be adjusted by the gross adjustment assembly and/or the fine adjustment assembly to vary the volume of the fresh sample taken into the sample chamber during each up stroke. The volume of the sample taken on the down stroke is determined by the volume of fresh sample taken into the volume chamber during the previous up stroke.

The sample chamber is sometimes referred to herein as a "variable volume sample chamber" because the distance of the up stroke of the sample head may be adjusted by the gross adjustment assembly and the fine adjustment assembly. The distance of the up stroke, which is adjustable, will control the volume of sample taken into the variable volume sample chamber.

BRIEF DESCRIPTION OF THE DRAWINGS

FIG. 2 is a section view of the liquid sample apparatus of FIG. 1 with the sample head assembly inserted in the liquid pipeline.

FIG. 3 is an enlarged section view of a portion of the insertion assembly showing the insertion piston and a portion of the insertion shaft of FIG. 1 in the withdrawn position of FIG. 1.

FIG. 4 is an enlarged section view of the sample head assembly of FIG. 1. This sample head assembly is designed to sample in a predetermined range of from less than 1 cc to 11 cc.

FIG. 5 is an enlarged section view of the first check valve assembly of FIG. 4. The first check valve assembly is shown in the closed position.

FIG. 6 is an enlarged section view of the second check valve assembly of FIG. 4. The second check valve assembly is shown in the closed position.

In FIG. 7, the first check valve assembly is in the open position with flow arrows indicating the direction of liquid flow. The first check valve assembly is only in the open position when the middle shaft 26 strokes up to allow fresh liquid to flow into the variable volume sample chamber 80 from the pipeline. When the first check valve assembly is open, the second check valve assembly is closed and vice a versa.

FIG. 10 is a section view of an alternative embodiment of the sample head assembly. This sample head is designed to sample in a predetermined range of from less than 1 cc to 24 cc.

FIG. 11 is an enlarged section view of the first check valve assembly of FIG. 10. In this view, the first check valve assembly is in the closed position.

FIG. 12 is an enlarged section view of the second check valve assembly of FIG. 12. In this view, the second check valve assembly is in the closed position.

FIG. 16 is a plan view of the removable adjustment pin.

FIG. 17 is a section view of the removable adjustment pin along the line 17-17 of FIG. 16.

FIG. 18 is a plan view of the tools that may be used to make adjustments to the fine adjustment wheels of FIG. 15.

FIG. 19 is an end view of one of the adjustment tools along line 19-19 of FIG. 18. These tools are circular in cross section.

FIG. 21 is an enlarged section view of the sample size adjustment assembly with the removable pin in the fourth set of adjustment apertures. In this view, the middle shaft travels through a minimum stroke.

FIG. 22 is an enlargement of the gap between the removable adjustment pin and the fine adjustment assembly of FIG. 21 showing the small amount of travel of the middle shaft during a minimum stroke of the sampler as indicated by the arrows. In this position, the sampler will take the minimum volume of sample in a predetermined range.

DETAILED DESCRIPTION OF THE INVENTION

Figure 1:
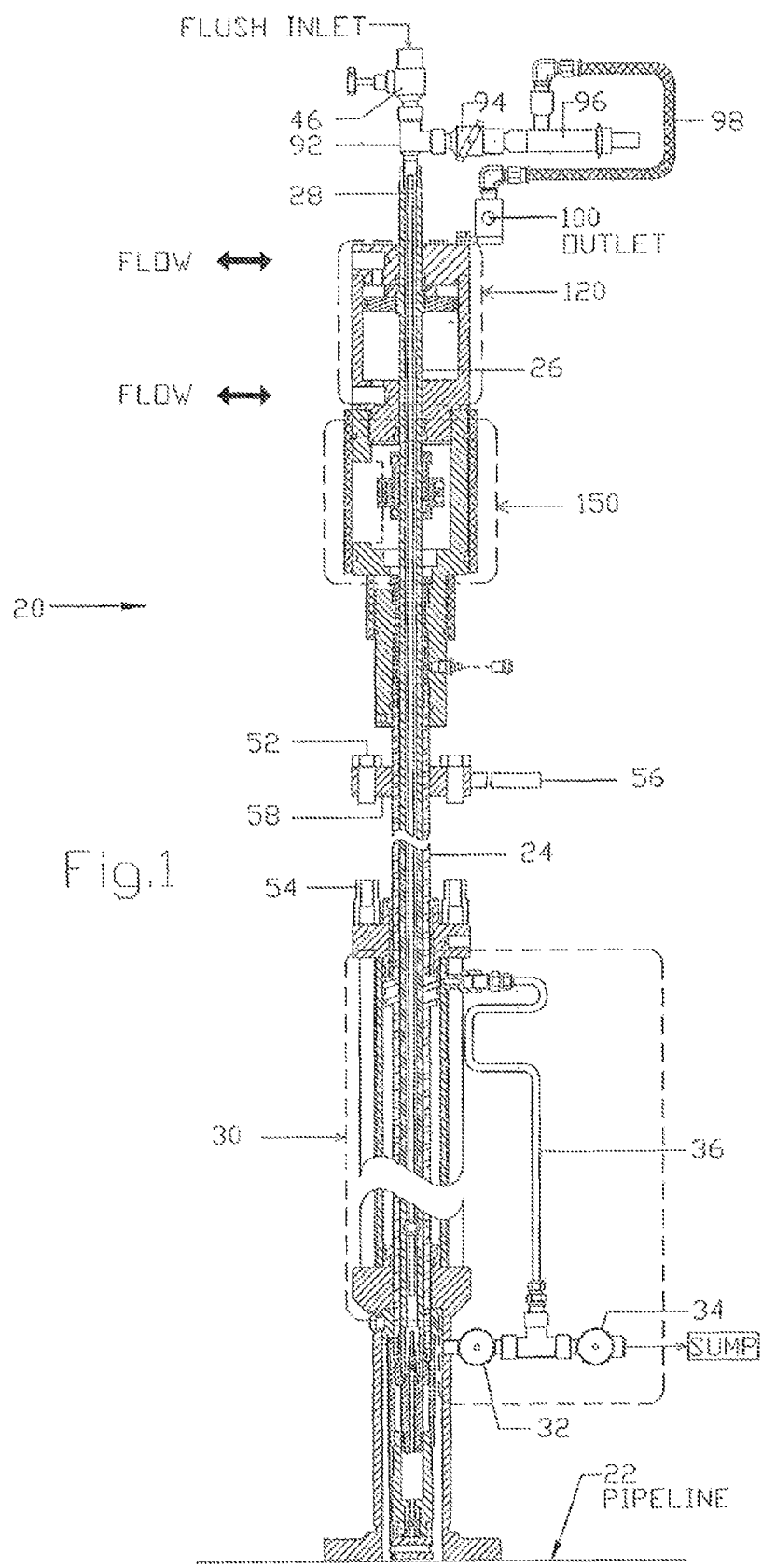
FIG. 1 is a section view of a liquid sample apparatus mounted on a liquid pipeline with the sample head assembly withdrawn from the liquid pipeline.

Referring now to FIGS. 1, 2 and 3, the liquid sampler is generally identified by the numeral 20 and is shown in section view. The sampler is designed to be installed on a liquid pipeline 22. Typically, the sampler connects to an isolation valve, not shown, which connects to the pipeline, as is well known to those skilled in the art. The isolation valve has been omitted from these drawings to save space and have more room to show the sampler 20. When the isolation valve is closed, the sampler may be removed from the isolation valve without having to shut down or otherwise depressurize the pipeline. The sampler 20 may be designed to operate at varying pressures and temperatures depending on the application. As an example, the sampler 20 could be built with a maximum allowable operating pressure of 285 PSIG and an allowable operating temperature range from −20° F. to +100° F. The sampler may also be designed for different operating pressures and temperatures for different applications.

The sampler includes three concentric tubes, better seen in FIG. 3: the insertion shaft 24, the middle shaft 26 and the flush tube 28, which run for a portion of the length of the liquid sampler. The sampler also includes an insertion assembly 30 identified by the dashed lines in FIG. 1. An enlarged portion of the insertion assembly is shown in section view in FIG. 3. The purpose of the insertion assembly 30 is to insert at least a portion of the sample head assembly 70, better seen in FIG. 4, into the pipeline as shown in FIG. 2 or to withdraw the entirety of the sample head assembly 70 from the pipeline as shown in FIG. 1. During normal operation, a portion of the sample head assembly 70 is inserted into the pipeline as shown in FIG. 2 in order to take samples of the product flowing through the pipeline.

Referring to FIG. 1, the insertion assembly 30 includes a first shut off valve 32, a second shut off valve 34, and tubing 36; in addition, an insertion piston 38 slides back and forth in an insertion cylinder 40. The insertion shaft 24 is attached to or is an integral part of the insertion piston 40. The insertion piston divides the insertion cylinder 38 into an upper fluid chamber 42 and a lower fluid chamber 44.

Referring now to FIGS. 1 and 3, in order to insert at least a part of the sampler into the pipeline, the second shut off valve 34 is closed and the first shut off valve 32 is opened. This allows the pressurized fluid from the pipeline to flow through the tubing 36 into the upper fluid chamber 42 which forces the insertion piston 38 towards the pipeline to insert at least a portion of the sample head assembly 70 in the pipeline as shown in FIG. 2.

In order to remove the entirety of the sampler from the pipeline, the first shut off valve 32 is closed, and the second shut off valve 34 is opened to bleed off the fluid pressure from the upper fluid chamber 42. The pipeline pressure will push the entire sampler out of the pipeline and back into the withdrawn position of FIG. 1.

An insertion shaft locking assembly 50 is shown by the dotted line in FIG. 2. In FIG. 1, the insertion shaft locking assembly 50 is in the disconnected position because the sampler is out of the pipeline. But in FIG. 2, the insertion shaft locking assembly 50 is in the locked position. A plurality of bolts 52, best seen in FIG. 1, fit through a plurality of openings in a lock collar 58. The lock collar 58 is permanently connected to the insertion shaft 24 and travels up and down with the movement of the insertion shaft. The bolts 52 are threaded into a plurality of lower bolt receptacles 54, thus securing the lock collar 58 to the lower bolt receptacles which secures the sampler in the pipeline against pipeline pressure. If the bolts are removed from the lower bolt receptacles 54, the sampler will be pushed from the pipeline by pipeline pressure as shown in FIG. 1. A direction indicator 56 shows the direction of the sample head assembly 70 to make sure the sampler is properly oriented to pipeline flow. Those skilled in the art will recognize that it is desirable for the pipeline owner/operator to be able to insert and withdraw the sampler from the pipeline without having to shut down or reduce pressure in the pipeline. In FIG. 3, a plurality of slotted bearings 142 surround the insertion shaft 24 to facilitate alignment and movement of a portion of the insertion shaft 24 in and out of the pipeline.

A sample head assembly is shown by the dotted line 70 in FIG. 2 and in enlarged section view in FIG. 4. A variable volume sample chamber 80 is positioned between the first check valve assembly 76 and the second check valve assembly 78. The size of the sample chamber may vary depending on the application. As an example, the variable volume sample chamber 80 in FIG. 4 was designed to hold about 11 cc; but other sizes can be manufactured using this invention. As another example, the variable volume sample chamber 86 in FIG. 10 holds about 24 cc. Other sizes are within the scope of this invention. In FIG. 4, slotted bearings 142 surround the middle shaft 26 to facilitate alignment and movement of the middle shaft 26 when the sampler is stroked up and down.

In FIG. 5, the first check valve assembly 76 is shown in an enlarged section view, and is shown in the closed, no-flow position. In FIG. 6, the second check valve assembly 78 is shown in an enlarged section view, and is also shown in the closed, no-flow position.

Figure 7:
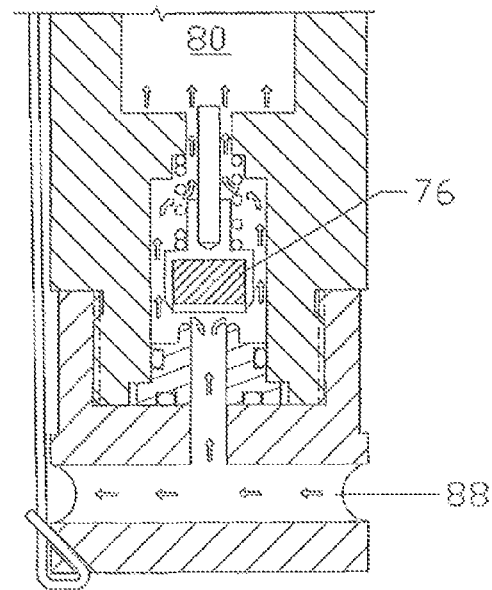
FIG. 7 is an enlarged section view of the first check valve assembly of FIG. 5.

In FIG. 7, the first check valve assembly 76 is shown in the open position; liquid flow is represented by the flow arrows. The first check valve assembly 76 opens when the sampler strokes up. The fluid moves from the pipeline 22, through the inlet 88, past the first check valve assembly 76, into the variable volume sample chamber 80.

Figure 8:
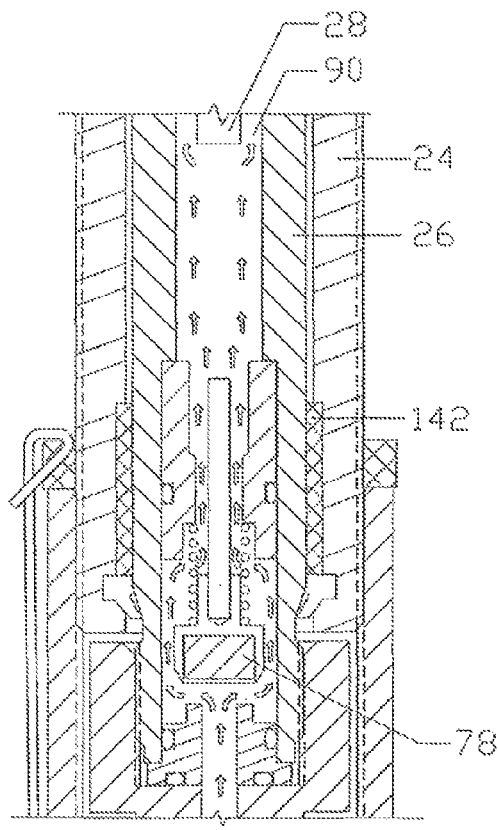
FIG. 8 is an enlarged section view of the second check valve assembly of FIG. 6. In this view, the second check valve assembly is in the open position with flow arrows indicating the direction of liquid flow up the annulus. The second check valve assembly is only in the open position when the middle shaft strokes down to take a sample.

During sampling, the shut off valve 46, better seen in FIG. 1, is in the closed position. In order to take a sample, the middle shaft 26 is stroked down causing the second check valve assembly 78 to open as shown in FIG. 8. Liquid sample is pumped from the variable volume sample chamber 80 up past the second check valve assembly 78 and up the annulus 90 as indicated by the flow arrows in FIGS. 8 and 9. As better seen in FIG. 2, the sample flows through an elbow 92, then through the third shut off valve 94, past a check valve 96, and through flexible tubing 98 and to the outlet 100. The sample is typically collected in a sample collection vessel/container 106. Once a sufficient volume of fluid is in the sample collection vessel/container, it may be taken to a laboratory for analysis or it may simply be held for archival purposes.

Figure 9:
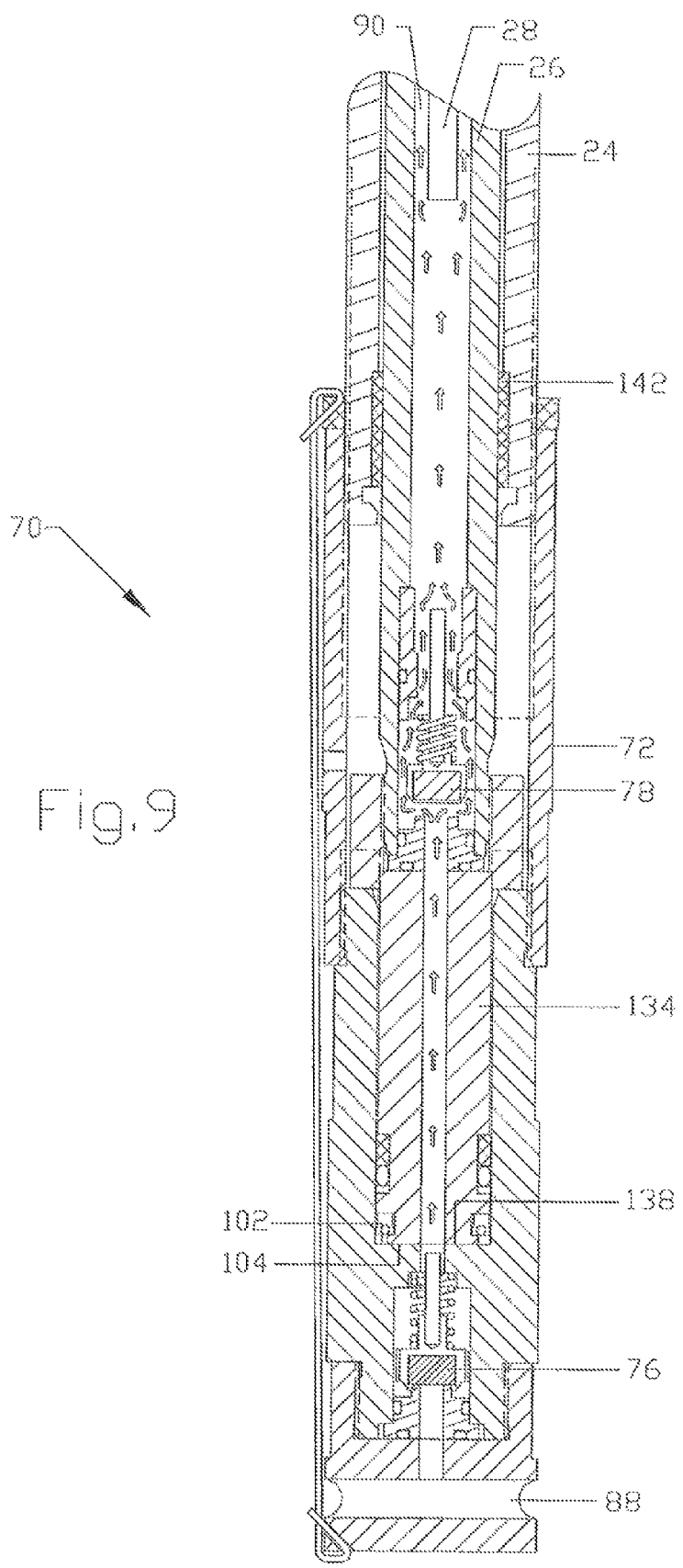
FIG. 9 is an enlarged section view of the sample head assembly of FIG. 4, except the sample head 134 is in the lower position. In this figure, the bottom surface 138 of the sample head 134 touches the bottom surface 104 of the variable volume sample chamber 80. When the middle shaft is traveling down towards the pipeline, to take a sample, the second check valve assembly is open as shown in this figure and the first check valve assembly is closed.

Referring now to FIG. 9, the sample head 134 is indirectly connected to the middle shaft 26 so the sample head travels up and down as the middle shaft is stroked up and down. During the down stroke, the second check valve assembly 78 opens and liquid flows from the variable volume sample chamber 80 up past the second check valve assembly 78 into the annulus 90 as shown by the flow arrows. At the conclusion of a down stroke of the sampler, the bottom surface 138 of the sample head 134 contacts the bottom surface 104 of the variable volume sample chamber 80 which limits the downward travel of the middle shaft 26 and the sample head assembly 134 as shown in this figure. It is desirable to fully pump all of the fluid out of the variable volume sample chamber 80 during each down stroke of the middle shaft 26 because there is no dead space or stale sample left in the variable volume sample chamber 80.

Referring now to FIG. 10, a section view of an alternative embodiment of the sample head assembly 74 is shown in section view. A first check valve assembly 82 is shown in section view in FIG. 11; in this view the first check valve assembly 82 is shown in the closed, no-flow position.

In FIG. 12, a second check valve assembly 84 is shown in section view, and in the closed no-flow position. A variable volume sample chamber 86 is positioned between the first check valve assembly 82 and the second check valve assembly 84. The size of the variable volume sample chamber 86 may vary according to the application. This particular chamber was sized to hold about 24 cc of liquid.

Figure 13:
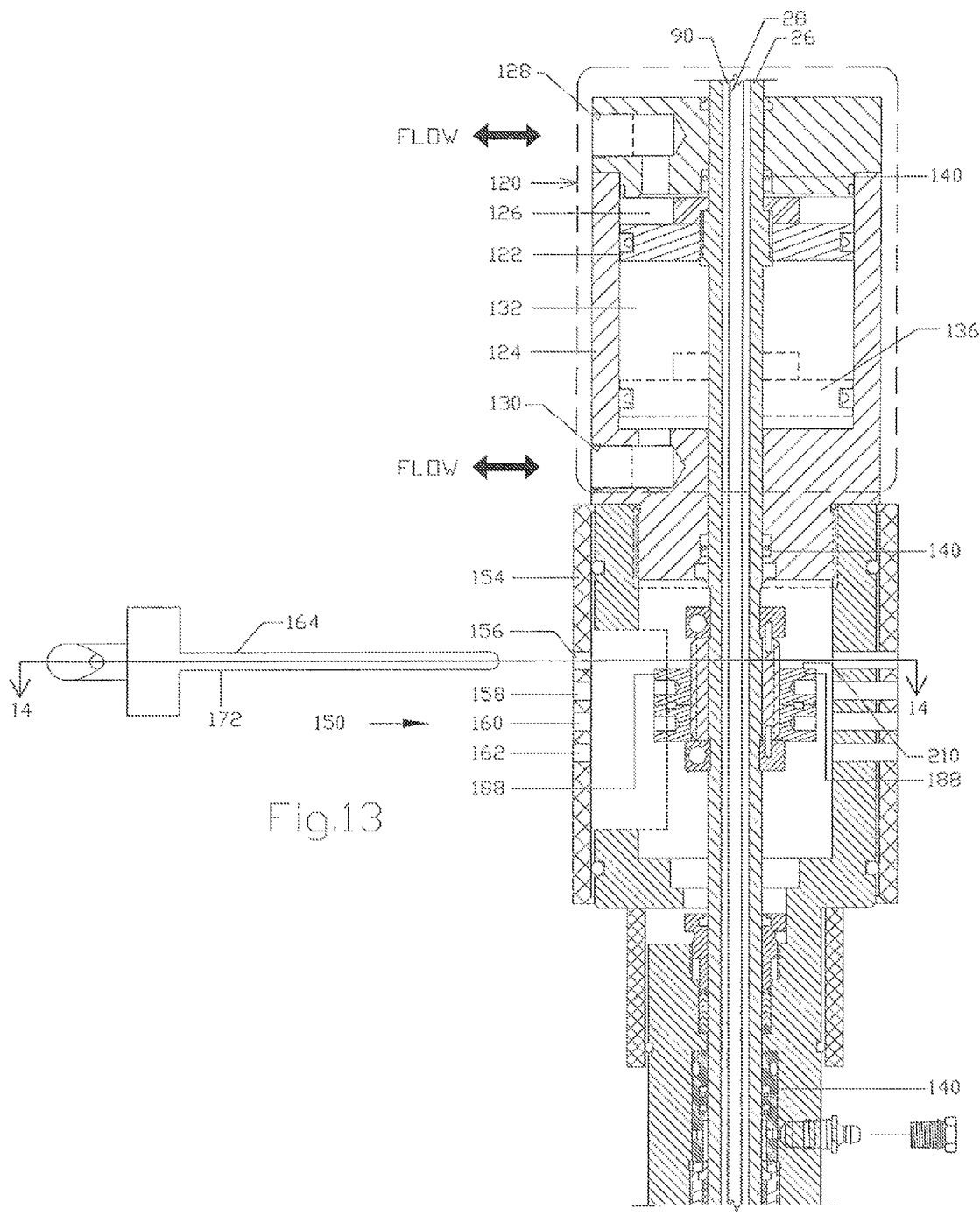
FIG. 13 is an enlarged section view of the sample actuation assembly and the sample adjustment assembly of FIG. 1.

Referring now to FIG. 13, the sample actuation assembly 120 is generally identified by the dashed line. The sample actuation assembly 120 includes an actuation piston 122 which slides up and down in an actuation cylinder 124 in response to opposing fluid forces acting on the actuation piston 122, which will be described below. In FIG. 13, the actuation piston 122 is shown in the upper position. The lower position 136 is shown in phantom. The actuation piston 122 divides the actuation cylinder 124 into an upper actuation fluid chamber 126 and a lower actuation fluid chamber 132. The upper actuation fluid chamber 126 is in fluid communication with an upper inlet/outlet port 128; the lower actuation fluid chamber 132 is in fluid communication with a lower inlet/outlet port 130. The upper inlet/outlet port 128 is connected to a hydraulic fluid pump not shown. The middle shaft 26 threadably connects to the actuation piston 122 at the upper end and indirectly connects to the sample head 134 at the lower end. When pressurized fluid passes through the upper inlet/outlet port 128, it fills the upper actuation fluid chamber 126 which forces the actuation piston 122 into the lower position 136 shown in phantom.

When the middle shaft 26 travels down in response to forces acting on the actuation piston 122, as best seen in FIG. 9, the sample head 134 travels down into the variable volume sample chamber 80. When the sample head 134 travels down into the variable volume sample chamber 80, the second check valve assembly 78 opens allowing a sample of liquid to flow up the annulus 90; the act of taking a sample as just described is sometimes called a "grab" in the industry. When the middle shaft 26 moves down, this is also referred to in the industry as a "down stroke". When fluid is bled from the upper actuation fluid chamber 126, the middle shaft 26 will travel up and out of the variable volume sample chamber 80. Further, as the sample head 134 travels up and out of the variable volume sample chamber 80, the first check valve assembly 76 will open allowing fresh liquid from the pipeline to flow past the first check valve assembly 76 and into the variable volume sample chamber 80.

Figure 15:
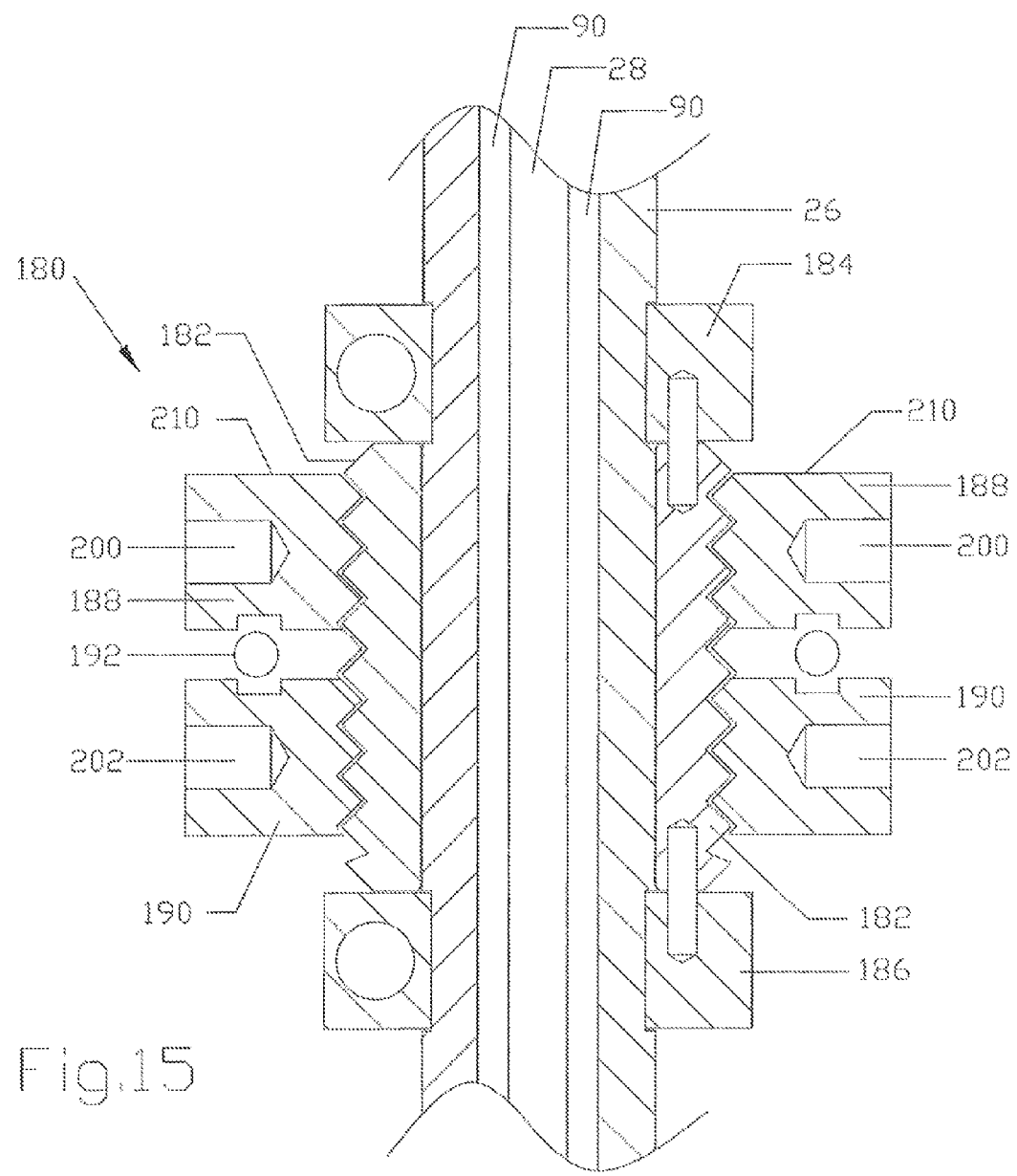
FIG. 15 is an enlarged section view of the fine adjustment assembly and a portion of the middle shaft. In this view, the upper locking ring is separated from the lower locking ring, solely for illustrative purposes to better show the structure. Unless being adjusted, the opposing locking rings are typically closer together as shown in FIG. 13.

The volume of sample may be adjusted by a sample adjustment assembly 150 indicated by the dashed line in FIG. 1. The sample adjustment assembly 150 includes a "gross adjustment" assembly 152. As an option, a "fine adjustment" assembly 180, as shown in FIG. 15, may also be added to the sample adjustment assembly 150. Both the gross adjustment assembly 152 and the fine adjustment assembly 180 are shown in section view in FIG. 13. The gross adjustment assembly 152 includes a cylindrical transparent Plexiglas® plastic housing 154.

Figure 14:
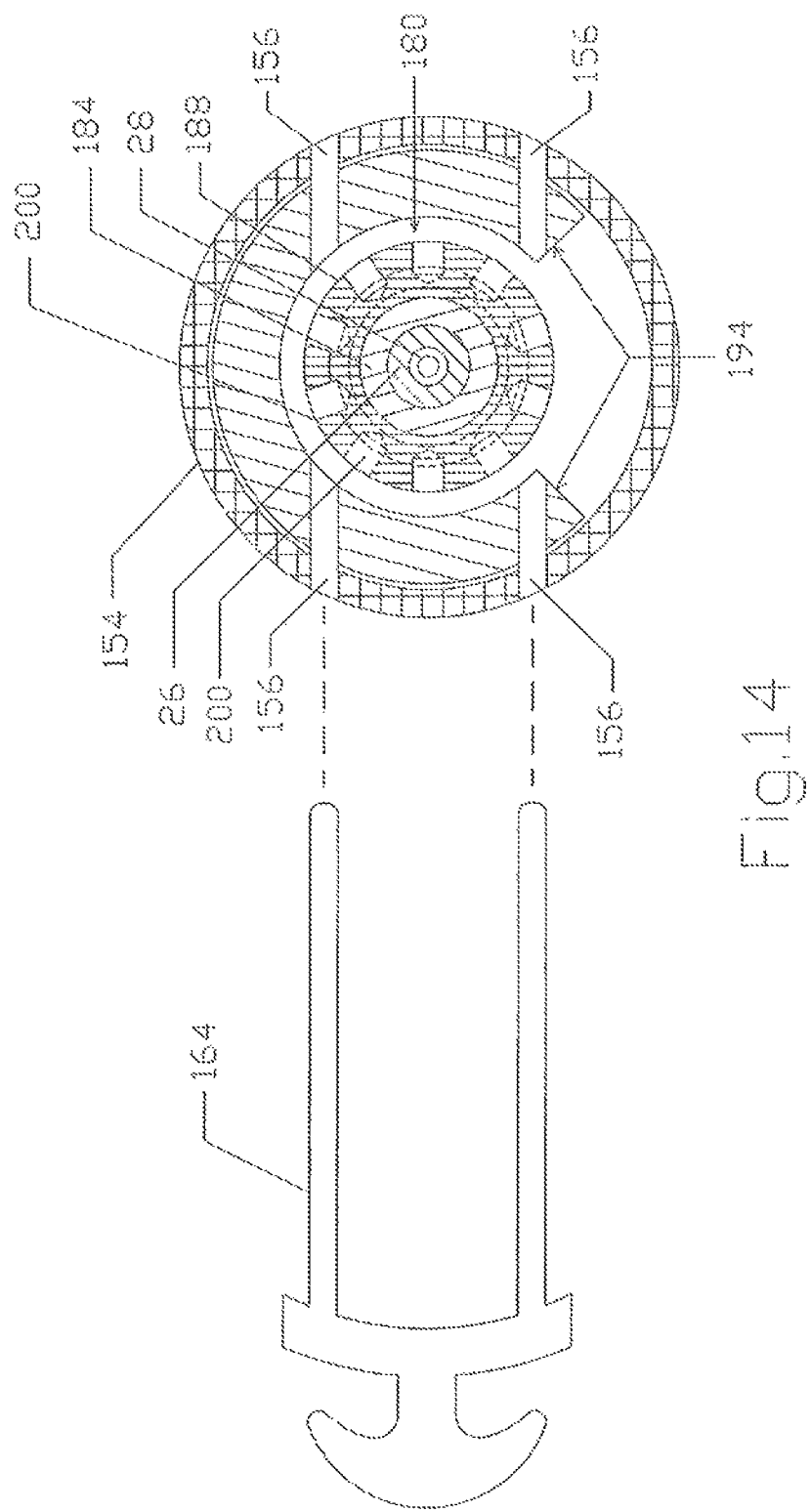
FIG. 14 is a section view along the line 14-14 of FIG. 13 showing the removable adjustment pin and the sample size adjustment assembly.
Figure 24:
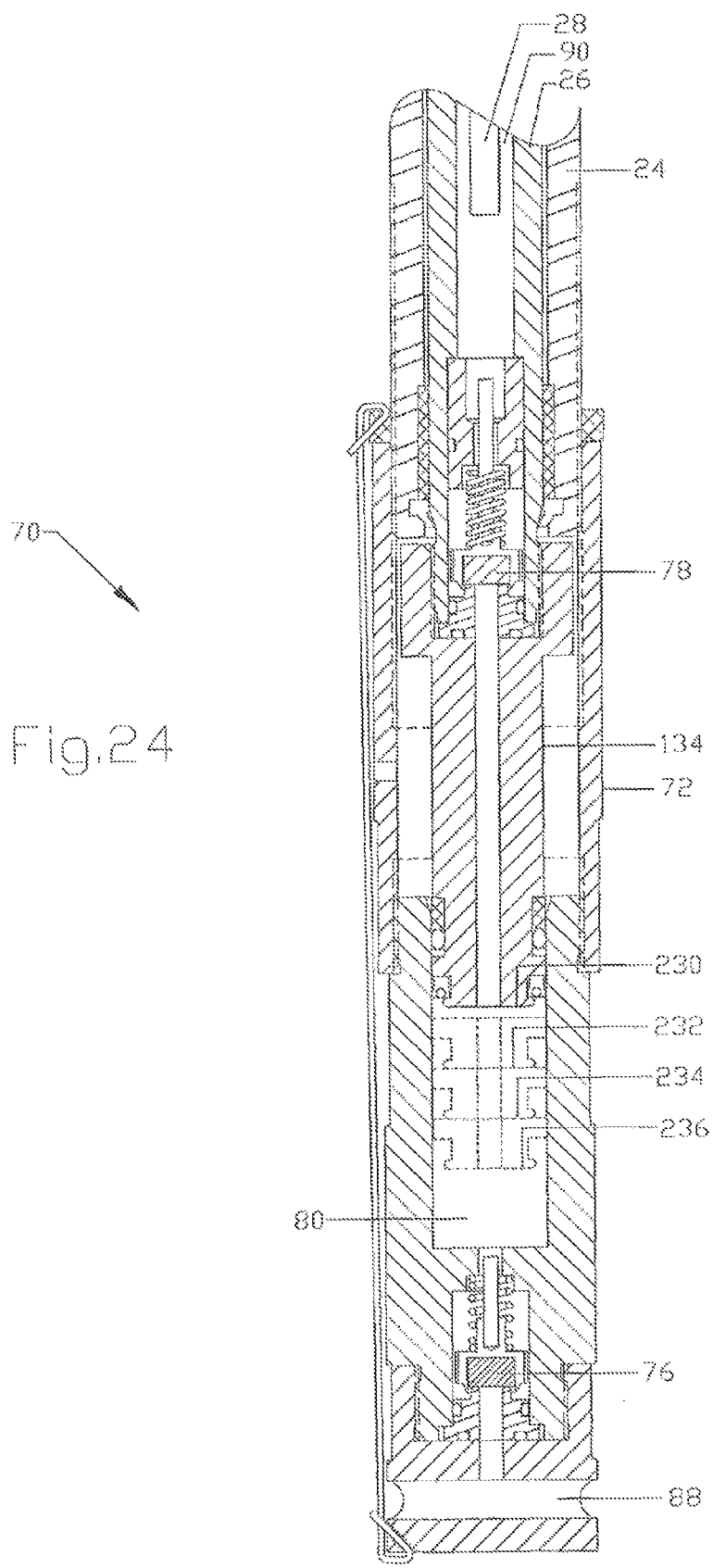
FIG. 24 is an enlarged section view of the sample head similar to FIG. 4, except the various positions of the sample head during the up stroke are shown in phantom. These various positions are selected by adjustment of the gross adjustment assembly.

Referring now to FIGS. 13 and 14, a removable adjustment pin 164 is shown in section view outside the cylindrical transparent Plexiglas® plastic housing 154. The removable adjustment pin 164 has two elongate prongs, as shown in FIG. 14. The removable adjustment pin 164 may be placed in different positions in the cylindrical transparent Plexiglas® plastic housing 154 to vary the stroke distance during the up stroke of the middle shaft, thus limiting the size of the variable volume sample chamber 80 and the amount of fresh liquid taken into the variable volume sample chamber 80 from the pipeline. The variable volume of the variable volume sample chamber 80 is best seen in FIG. 24.

The number of adjustment pin positions is determined by the application and/or the customer. In this example in FIG. 13, the pin may be set in any of four different positions. But in another application, five or more pin positions may be necessary. Or in the alternative, only three or fewer pin positions may be necessary in some other application.

The position of the removable adjustment pin 164 is determined by a set of adjustment apertures formed in the cylindrical transparent Plexiglas® plastic housing 154. In this example, the four sets of adjustment apertures are shown. The first set of adjustment apertures 156 are arranged in the upper most position in the cylindrical transparent Plexiglas® plastic housing 154. This first set of adjustment apertures 156 are sized and arranged to receive the elongate prongs of the removable adjustment pin 164, as are all the other adjustment apertures described hereinafter. Each set of adjustment apertures includes four openings aligned on a parallel axis to receive the elongate prongs of the removable adjustment pin 164.

Below the first set of adjustment apertures 156 are a second set of adjustment apertures 158. Below the second set of adjustment apertures 158 are a third set of adjustment apertures 160. Below the third set of adjustment apertures 160 are a fourth set of adjustment apertures 162. As can be seen from FIG. 13, the removable adjustment pin 164 can only be inserted into one set of adjustment apertures at a time.

When the removable adjustment pin 164 is inserted in the first set of adjustment apertures 156, the middle shaft 26 has maximum up travel and the sampler will take in approximately 11 cc of sample into the variable volume sample chamber 80, in this embodiment. The embodiments can be varied to adjust the amount of total sample taken during a maximum stroke. When the removable adjustment pin 164 is inserted in the second set of adjustment apertures 158, the middle shaft 26 has a shorter distance of up travel and the sampler will take approximately 8 cc of fresh sample into the variable volume sample chamber 80 during each up stroke. When the removable adjustment pin 164 is inserted in the third set of adjustment apertures 160, the middle shaft 26 has even less travel and the sampler will take approximately 5 cc of fresh sample each time the sampler strokes up. When the removable adjustment pin 164 is in the fourth set of adjustment apertures 162, the middle shaft 26 has the minimum amount of travel and will take approximately 2 cc of fresh sample into the variable volume sample chamber 80 every time the sampler strokes up.

Hydraulic fluid introduced into the sample actuation assembly 120 causes the actuation piston 122 to travel up and down in the actuation cylinder 124. But the distance of travel of the middle shaft 26 is not limited by the travel of the actuation piston 122. Rather, the distance of up travel of the middle shaft 26 is determined by the gross adjustment assembly 152 and optionally by the fine adjustment assembly 180. The sampler shown in these drawings has both the gross adjustment assembly 152 and the fine adjustment assembly 180, but not all embodiments of the invention have the fine adjustment assembly 180.

Referring now to FIGS. 13 and 9, the upper limitation of the gross travel distance of the middle shaft 26 is determined by the location of the removable adjustment pin 164 in the cylindrical transparent Plexiglas® housing 154. When the actuation piston 122 is in the upper position as shown in FIG. 13, the upper surface 210 of the upper lock ring 188 is stopped by the bottom surface 172 of the removable adjustment pin 164. When the actuation piston 122 is stroked down, the actuation piston 122 moves to the lower position 136 as shown in phantom in FIG. 13. In this position, the travel of the middle shaft 26 is stopped when the bottom surface 138 of the sample head 134 contacts the bottom surface 104 of the variable volume sample chamber 80 as better seen in FIG. 9. A plurality of Poly Pak™ seals 140 surround the middle shaft 26 above and below the sample actuation assembly 120. These Poly Pak™ seals 140 also surround the middle shaft 26 below the sample adjustment assembly 150. Poly Pak™ seals are available from Parker Hannifin Corp. of Haverhill, Mass. (www.parker.com).

Referring now to FIGS. 14 and 15, the fine adjustment assembly is generally identified by the numeral 180. This fine adjustment assembly 180 is used to make fine adjustments in the volume of sample; these adjustments are more precise than those that can be made by the removable adjustment pin 164. Access to the fine adjustment assembly 180 is through an access window 194 in the cylindrical transparent Plexiglas® housing 154. The fine adjustment assembly 180 includes a barrel 182, which is not threaded on the inside diameter but is threaded on the outside diameter. The barrel 182 may be locked in place on the middle shaft 26 by an upper locking lug 184 and a lower locking lug 186; the exterior of the barrel 182 is threaded, as shown in FIG. 15. An upper locking ring 188 and a lower locking ring 190 are threaded on the inside diameter and are sized and arranged to threadably engage the threaded exterior of the barrel 182. A plurality of adjustment openings 200 are radially arranged along the outside circumference of the upper locking ring 188. The diameter of each adjustment opening is the same. The size of each adjustment opening 200 is sized and arranged to receive and engage with either of the tools shown in FIG. 18. A plurality of adjustment openings 202 are radially arranged along the outside circumference of the lower locking ring 190. The diameter of the adjustment openings 200 and 202 are the same. Each of the adjustment openings 202 are sized and arranged to receive and engage with either of the tools shown in FIG. 18.

In order to adjust the fine adjustment assembly 180, both tools are inserted through the access window 194. Tool 196 may be inserted in one of the plurality of adjustment openings 202 in the lower locking ring 190. Tool 198 may be inserted in one of the plurality of adjustment openings 200 in the upper locking ring 188. Clockwise movement of the tool 196 moves the lower locking ring 190 down; counter-clockwise movement of the tool 196 moves the lower locking ring 190 upward, away from the pipeline. Clockwise movement of the tool 198 moves the upper locking ring 188 down; counter-clockwise movement of the tool 198 moves the upper locking ring 188 upward, away from the pipeline. In this fashion, the upper and lower locking rings, 188 and 190 respectively, may be moved up or down relative to the barrel 182. After adjustment, the locking rings 188 and 190 are tightened against each other to releasably lock the rings at a desirable location on the barrel 182.

In FIG. 15, when the locking rings, 188 and 190, are rotated up, which is away from the pipeline, the volume of the sample is slightly decreased. When the locking rings, 188 and 190, are rotated down as shown in FIG. 13, the volume of the sample is slightly increased. (Down is towards the pipeline).

An O-ring 192 is positioned between the upper locking ring 188 and the lower locking ring 190; the purpose of the O-ring 192 is not to provide a seal. Rather, the O-ring 192 is used in this application as a resilient spring which will exert force on both locking rings 188 and 190 to releasably lock the two locking rings, 188 and 190, together when tightened by the tools, 196 and 198, shown in FIGS. 18 and 19. Applicant has determined than a Buna-N O-ring with a Shore D 90 Durometer hardness is suitable for this application. Other O-rings may function in this application, such as a Viton® O-ring, provided that the O-ring is stiff enough to act as a spring and not be permanently deformed when the locking rings 188 and 190 are tightened against each other.

Figure 20:
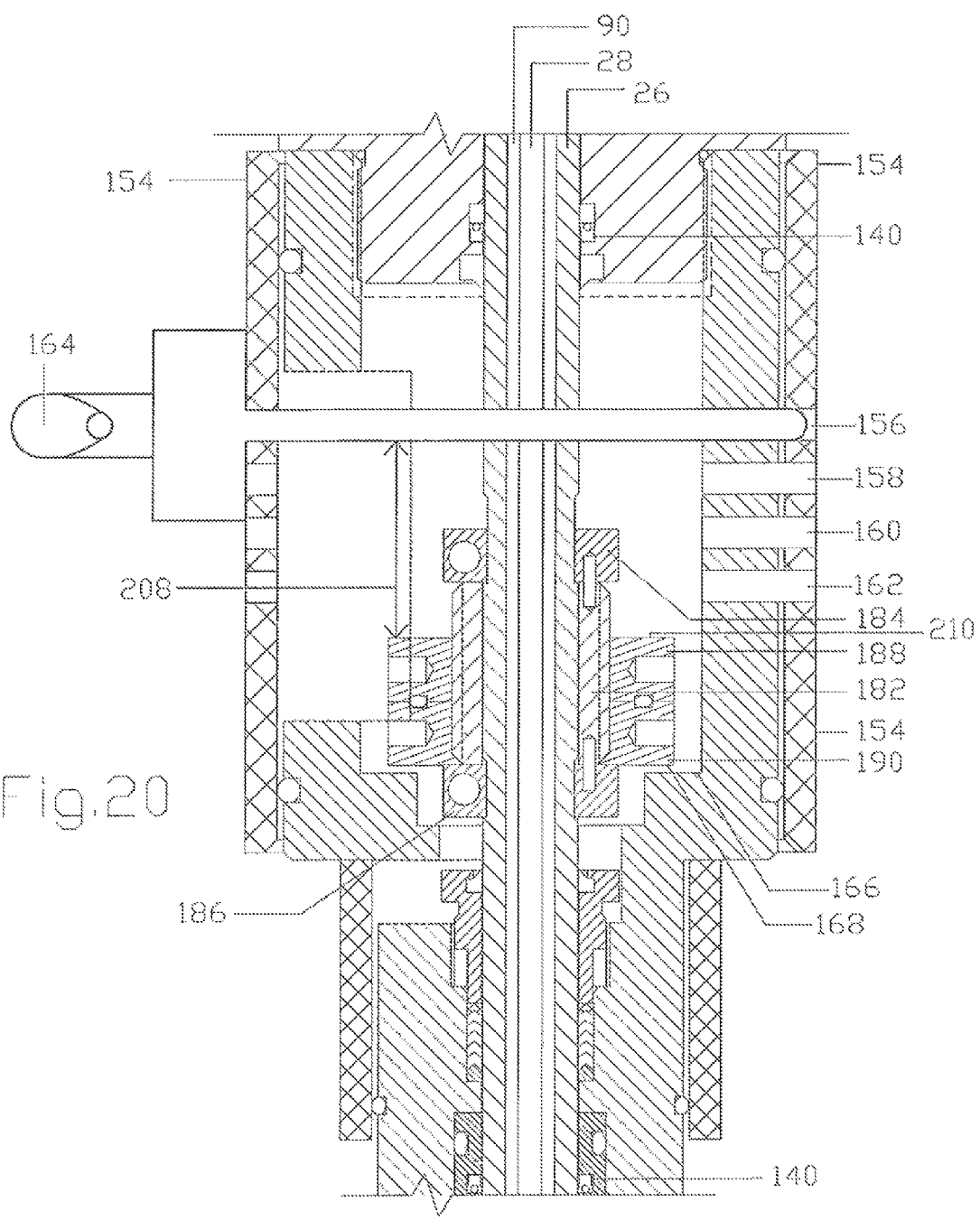
FIG. 20 is an enlarged section view of the sample adjustment assembly with the adjustment pin in the first set of adjustment apertures. In this view, the middle shaft travels through a maximum stroke as indicated by the arrows. In this position, the sampler can take the maximum volume of sample in the predetermined range.

FIG. 20 is an enlarged section view of the sample adjustment assembly 150 with the removable adjustment pin 164 in the first set of adjustment apertures 156. In this view, the middle shaft 26 travels through a maximum stroke up and down as indicated by the arrows 208. In this position, the sampler can take the maximum volume of sample in the predetermined range. The length of the stroke of the middle shaft 26 in FIG. 20 is from the bottom surface 172 of the removable adjustment pin 164 to when the sample head 134 touches the bottom surface 104 of the variable volume sample chamber 80 as better seen in FIG. 9.

FIG. 21 is an enlarged section view of the sample adjustment assembly 150 with the removable adjustment pin 164 in the fourth set of adjustment apertures 162 and FIG. 22 is an enlargement of the gap between the bottom surface 172 of the removable adjustment pin 164 and the top surface 210 of the upper lock ring 188. In these views, the middle shaft 26 travels through a minimum stroke up and down as indicated by the arrows 206. In this position the sampler will take the minimum volume of sample in the predetermined range. The length of the down stroke of the middle shaft 26 in FIGS. 21 and 22 is from the bottom surface 172 of the removable adjustment pin 164 to when the sample head 134 touches the bottom surface 104 of the variable volume sample chamber 80 as better seen in FIG. 9.

FIG. 22 is an enlargement of the gap between the bottom surface of the 172 of the removable adjustment pin 164 and the top surface 210 of the upper lock ring 188. The bottom surface 168 of the lower lock ring 190 does not contact the housing shoulder 166. Rather, the travel of the middle shaft 26 is limited on the down stroke when the sample head 134 touches the bottom surface 104 of the variable volume sample chamber 80 as better seen in FIG. 9.

Figure 23:
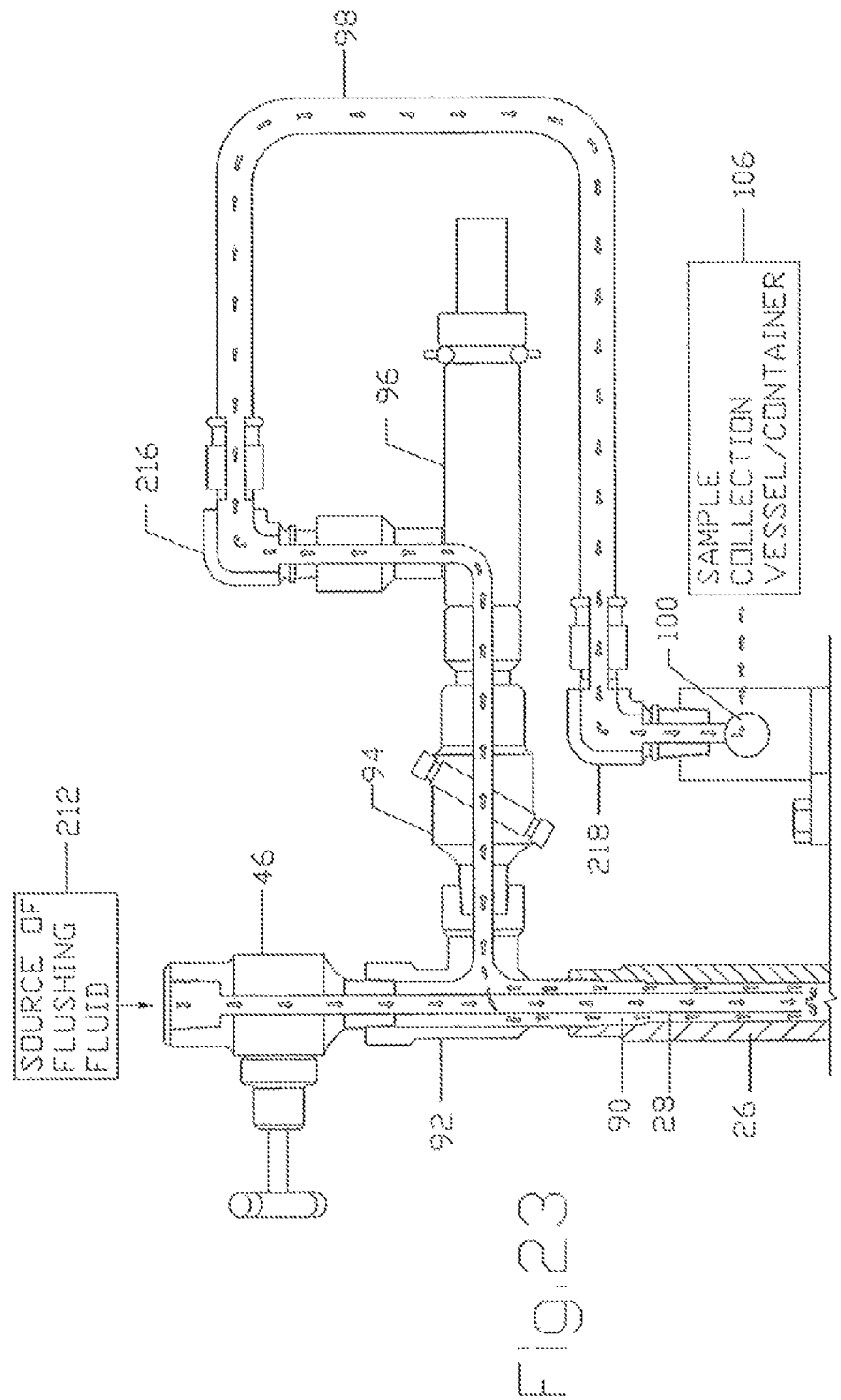
FIG. 23 is an enlarged section view of the flushing fluid flowing through a portion of the sampler 20.

FIG. 23 is a section view of the shut off valve 46 where it contacts the first elbow 92 and related equipment on the upper end of the sampler 20. Flushing may not be done while sampling; but flushing may be done while the sample head assembly 70 is withdrawn from the pipeline as shown in FIG. 1 or when a portion of the sample head assembly 70 is inserted in the pipeline as shown in FIG. 2. A flushing fluid may be a liquid such as the product flowing through the pipeline or a gas such as nitrogen. Nitrogen is preferred. In order to flush the sampler, the shut off valve 46 is opened and the flushing fluid is pumped from a source of flushing fluid 212 through the shut off valve 46 down through the flush tube 28 (towards the pipeline). At the end of the flush tube 28, the flushing fluid changes directions and flows up the annulus 90 through the first elbow 92, the third shut off valve 94, past the check valve 96, through the elbow 216, through the flexible tubing 98, through the elbow 218, and exits the outlet 100 into a removable flushing fluid sample collection vessel/container 106.

Flushing of the liquid sampler may be done as often as the operator requires. Typically, flushing occurs when the product in the pipeline changes from one product to another. As an example, flushing may occur when the fluid pipeline is being switched from gasoline to diesel. Flushing may also be done when product from one customer is switched to product from another.

FIG. 24 is a section view of the sample head assembly 70 similar to FIG. 4, except the various positions of the sample head 134 are shown in phantom. The volume of the variable volume sample chamber 80 is about 11 cc maximum, but the volume of the sample size can vary depending on the position of the gross adjustment assembly 152 and optionally by the fine adjustment assembly 180. When the sample head 134 is stroked up, the first check valve assembly 76 opens and fresh sample is drawn into the variable volume sample chamber 80; during the up stroke, the second check valve assembly 78 is closed. The volume of the fresh sample is determined by the position where the sample head 134 comes to rest in the variable volume sample chamber 80 during the up stroke, which can vary as shown in this figure. The variable position of the sample head assembly 70 is determined by the distance of travel of the middle shaft 26 during the up stroke which is limited by the position of the removable adjustment pin 164 in the gross adjustment assembly 152 and as may be further varied by the optional fine adjustment assembly 180. On the down stroke, the first check valve assembly 76 closes and the second check valve assembly 78 opens allowing the sample in the variable volume sample chamber 80 to be pumped up the annulus 90 as shown elsewhere. The distance of the down stroke stops when the sample head 134 bottoms in the variable volume sample chamber 80 better seen in FIG. 9.

When the removable adjustment pin 164 is in the first adjustment apertures 156, as better seen in FIG. 20, the middle shaft 26 travels its maximum distance during an up stroke, and the sample head 134 comes to rest at position 230. At position 230, the sampler will take about 11 cc of fresh sample into the variable volume sample chamber 80. On the down stroke, the 11 cc of fresh sample will be pumped past the second check valve assembly 78 and up the annulus 90.

When the removable adjustment pin 164 is in the second adjustment apertures 158 as better seen in FIG. 13, the middle shaft 26 travels less during the up stroke and the sample head 134 comes to rest at position 232. At position 232, the sampler will take about 8 cc of fresh sample into the sample collection chamber 80. On the down stroke, the 8 cc of fresh sample will be pumped past the second check valve assembly 78 and up the annulus 90.

When the removable adjustment pin 164 is in the third adjustment apertures 160, as better seen in FIG. 13, the middle shaft 26 travels even less during the up stroke and the sample head 134 comes to rest at position 234. At position 234, the sampler will take about 5 cc of fresh sample into the variable volume sample chamber 80. On the down stroke, the 5 cc of fresh sample will be pumped past the second check valve assembly 78 and up the annulus 90.

When the removable adjustment pin 164 is in the fourth adjustment apertures 162, as better seen in FIG. 21, the middle shaft 26 travels a minimum distance during the up stroke and the sample head 134 comes to rest at position 236. At position 236, the sampler will take about 2 cc of fresh sample into the variable volume sample chamber 80. On the down stroke, the 2 cc of fresh sample will be pumped past the second check valve assembly 78 and up the annulus 90. The distance the sample head moves during the up stroke defines the volume of the collection chamber and the volume of the fresh sample taken into the sample variable volume chamber 80. The positions 232, 234 and 236 are for illustrative purposes only and not meant to be the same scale or size of the arrows 206 and 208 in prior figures.

The invention claimed is:

1. A sample adjustment assembly associated with a pipeline, said assembly comprising:
    an adjustment pin;
    a housing including two or more adjustment apertures therein, wherein each aperture is sized and positioned to selectively received said adjustment pin;
    a shaft extending through the housing for axial movement therewithin downwardly toward said pipeline and upwardly away from said pipeline, said shaft oriented perpendicularly to the adjustment pin when said adjustment pin is positioned in an aperture of the housing;
    a lock ring secured on the shaft for movement therewith within the housing, wherein said lock ring is positioned on the shaft below said adjustment pin when said adjustment pin is positioned in an aperture of the housing such that said adjustment pin restricts upward travel of the lock ring, and thereby restricts upward axial travel of the shaft.

2. The sample adjustment assembly of claim 1 further including:
    a barrel connected with the shaft, said barrel having a threaded exterior;
    wherein said lock ring screws onto the barrel via the threaded exterior of the barrel, and wherein the lock ring can be rotated to raise or lower its position relative to the shaft to act as a fine adjustment mechanism.

3. The sample adjustment assembly of claim 2 further including:
    a second lock ring which is screwed onto the barrel; and
    an O-ring positioned between the lock ring and the second lock ring.

4. The sample adjustment assembly of claim 1 wherein the adjustment pin includes two prongs, and each said adjustment aperture includes two holes sized and positioned to receive the two prongs of the adjustment pin.

5. The sample adjustment assembly of claim 1 wherein each said adjustment aperture includes four holes, with two on each side of the housing, each sized and positioned to receive a prong of the adjustment pin.

6. The sample adjustment assembly of claim 1 wherein the number of adjustment apertures is at least four.

7. The sample adjustment assembly of claim 1 wherein placement of the adjustment pin in a lower adjustment aperture results in a shorter upward travel distance of the shaft.

8. A sampler associated with a pipeline, said sampler comprising:
    a sample head assembly including a variable volume sample chamber into which a sample head is selectively moveable;
    an insertion assembly including an insertion piston for selectively extending at least a portion of the sample head assembly into said pipeline for sampling;
    a sample adjustment assembly including:
        a housing and an adjustment pin, wherein the adjustment pin can be inserted into the housing in at least two positions;
        a middle shaft associated with the sample head for causing movement of the sample head, said middle shaft extending through the housing for axial movement therewithin downwardly toward said pipeline and upwardly away from said pipeline; and
        a lock ring secured on the shaft for movement therewith within the housing, wherein said lock ring is positioned on the shaft below said adjustment pin when said adjustment pin is positioned in an aperture of the housing; and
    a sample activation assembly including an actuation piston associated with the middle shaft;
    wherein upward movement of the actuation piston causes upward movement of the middle shaft and thereby of the sample head to allow the variable volume sample chamber to fill with a volume from the pipeline,
    wherein upward movement of the middle shaft and sample head is restricted by abutment of the lock ring with the adjustment pin in the housing, such restriction of upward movement of the sample head thereby determining the volume obtained within the variable volume sample chamber;
    wherein downward actuation of the actuation piston causes downward movement of the middle shaft and sample head, said downward movement of the sample head forcing the volume from the variable volume sample chamber toward a sample collection vessel.

9. The sampler of claim 8, wherein the insertion assembly includes:
    a first shutoff valve in fluid communication with the pipeline at a first side of the first shutoff valve;
    a second shutoff valve in fluid communication with a second side of the first shutoff valve; and tubing, a first end of which is in fluid communication with both the second side of the first shutoff valve and the second shutoff valve, and a second end of which is in fluid communication with the insertion piston;

wherein opening the first shutoff valve and closing the second shutoff valve allows pressurized fluid to flow through the first shutoff valve and through the tubing to pressurize and actuate the insertion piston, causing the insertion piston to force at least a portion of the sample head assembly into the pipeline; and wherein closing the first shutoff valve and opening the second shutoff valve allows pressure to bleed from the insertion piston, allowing the sample head assembly to withdraw from the pipeline.

10. The sampler of claim 8, further including a shaft locking assembly comprising:

an insertion shaft associated with the insertion piston, such that actuation of the insertion piston causes axial movement of the insertion shaft, which in turn causes selectively extending of at least a portion of the sample head assembly into said pipeline for sampling;

a lock collar connected with the insertion shaft, said lock collar including at least one bolt openings; and lower bolt receptacles for receiving bolts which pass through the bolt openings of the lock collar for retaining the sample head assembly within the pipeline.

11. The sampler of claim 8, wherein the variable volume chamber is sized to hold between about 0.5-cc to about 24-cc of fluid.

12. The sampler of claim 8, further including a first check valve for allowing fluid from the pipeline into the variable volume sample chamber, but preventing fluid from exiting back into the pipeline.

13. The sampler of claim 8, further including a second check valve for allowing fluid to leave the variable volume sample chamber toward the collection vessel, but preventing fluid from flowing back from the collection vessel into the variable volume sample chamber.

14. The sampler of claim 8, wherein the downward movement of the sample head causes the sample head to contact a bottom surface of the variable volume sample chamber, thereby limiting the downward travel of the middle shaft and sample head.

15. The sampler of claim 8 further including:

a barrel connected with the middle shaft, said barrel having a threaded exterior;

wherein said lock ring screws onto the barrel via the threaded exterior of the barrel, and wherein the lock ring can be rotated to raise or lower its position relative to the middle shaft to act as a fine adjustment mechanism.

16. The sampler of claim 15 further including:

a second lock ring which is screwed onto the barrel; and an O-ring positioned between the lock ring and the second lock ring.

17. The sampler of claim 8 wherein the adjustment pin includes two prongs, and the housing includes at least two adjustment apertures, with each said adjustment aperture including two holes sized and positioned to receive the two prongs of the adjustment pin.

18. The sampler of claim 17 wherein each said adjustment aperture includes four holes, with two on each side of the housing, each sized and positioned to receive a prong of the adjustment pin.

19. The sampler of claim 8 wherein the number of positions for the adjustment pin in the housing is at least four.

20. The sampler of claim 8 wherein placement of the adjustment pin in a lower position of the housing results in a shorter upward travel distance of the middle shaft.

21. A sampler associated with a pipeline, said sampler comprising:

an insertion shaft including an insertion piston, wherein actuation of the insertion piston causes axial movement of the insertion shaft;

a sample head assembly including a variable volume sample chamber into which a sample head is selectively moveable, wherein downward movement of the insertion shaft toward the pipeline causes movement of the sample head assembly at least partially down into the pipeline;

a middle shaft associated with the sample head and with an actuation piston, wherein actuation of the actuation piston causes axial movement of the middle shaft which in turn causes movement of the sample head within the variable volume chamber;

a lock ring secured on the middle shaft for movement therewith within a housing through which the middle shaft extends;

an adjustment pin selectively positionable at multiple positions within said housing, said adjustment pin variably limiting upward movement of the lock ring and middle shaft based on the position of the adjustment pin within the housing, such limiting of upward movement of the middle shaft thereby determining the upward movement of the sample head and the volume obtained within the variable volume sample chamber.

22. The sampler of claim 21, wherein the insertion assembly includes:

a first shutoff valve in fluid communication with the pipeline at a first side of the first shutoff valve;

a second shutoff valve in fluid communication with a second side of the first shutoff valve; and tubing, a first end of which is in fluid communication with both the second side of the first shutoff valve and the second shutoff valve, and a second end of which is in fluid communication with the insertion piston;

wherein opening the first shutoff valve and closing the second shutoff valve allows pressurized fluid to flow through the first shutoff valve and through the tubing to pressurize and actuate the insertion piston, causing the insertion piston to force at least a portion of the sample head assembly into the pipeline; and wherein closing the first shutoff valve and opening the second shutoff valve allows pressure to bleed from the insertion piston, allowing the sample head assembly to withdraw from the pipeline.

23. The sampler of claim 21, further including a shaft locking assembly comprising:

a lock collar connected with the insertion shaft, said lock collar including at least one bolt openings; and lower bolt receptacles for receiving bolts which pass through the bolt openings of the lock collar for retaining the sample head assembly within the pipeline when the actuation piston causes the insertion shaft to force the sample head assembly at least partially into the pipeline.

24. The sampler of claim 21, wherein the variable volume chamber is sized to hold between about 0.5-cc to about 24-cc of fluid.

25. The sampler of claim 21, further including a first check valve for allowing fluid from the pipeline into the variable volume sample chamber, but preventing fluid from exiting back into the pipeline.

26. The sampler of claim 21, further including a second check valve for allowing fluid to leave the variable volume sample chamber toward a collection vessel, but preventing fluid from flowing back from the collection vessel into the variable volume sample chamber.

27. The sampler of claim 21, wherein the downward movement of the sample head causes the sample head to contact a bottom surface of the variable volume sample chamber, thereby limiting the downward travel of the middle shaft and sample head.

28. The sampler of claim 21 further including:
a barrel connected with the middle shaft, said barrel having a threaded exterior;
wherein said lock ring screws onto the barrel via the threaded exterior of the barrel, and wherein the lock ring can be rotated to raise or lower its position relative to the middle shaft to act as a fine adjustment mechanism.

29. The sampler of claim 28 further including:
a second lock ring which is screwed onto the barrel; and
an O-ring positioned between the lock ring and the second lock ring.

30. The sampler of claim 21 wherein the adjustment pin includes two prongs, and the housing includes at least two adjustment apertures, with each said adjustment aperture including two holes sized and positioned to receive the two prongs of the adjustment pin.

31. The sampler of claim 30 wherein each said adjustment aperture includes four holes, with two on each side of the housing, each sized and positioned to receive a prong of the adjustment pin.

32. The sampler of claim 21 wherein the number of positions for the adjustment pin in the housing is at least four.

33. The sampler of claim 21 wherein placement of the adjustment pin in a lower position of the housing results in a shorter upward travel distance of the middle shaft.

* * * * *